United States Patent [19] [11] Patent Number: 4,923,965
Andruszkiewicz et al. [45] Date of Patent: May 8, 1990

[54] TRIPEPTIDES OF N[3]-4-METHOXYFUMARYL-L-2,3-DIAMINO-PROPANOIC ACID

[75] Inventors: Ryszard Andruszkiewicz, Sopot; Henryk Chmara, Gda sk; Slawomir Milewski, Gda sk; Edward Borowski, Gda sk; Maria Zaremba, Bialystok; Jerzy Borowski, Bialystok, all of Poland

[73] Assignee: Politechnika Gdanska, Gda sk, Poland

[21] Appl. No.: 222,190

[22] Filed: Jul. 21, 1988

[51] Int. Cl.[5] ................. A61K 37/02; C07K 5/08
[52] U.S. Cl. ...................................... 530/331
[58] Field of Search ................ 530/331; 514/18

[56] References Cited

U.S. PATENT DOCUMENTS 4,727,062 2/1988 Taub et al. .................. 530/331

OTHER PUBLICATIONS

J. Med. Chem. 30, 1715–1719, (1987) Andruszkiewicz et al., Synthesis and Biological Properties of N[3]-(4-Methoxyfumaroyl)-L-2,3-diaminopropanoic Acid Dipeptides.

Primary Examiner—Lester L. Lee
Attorney, Agent, or Firm—Ladas & Parry

[57] ABSTRACT

The subject of this present invention is tripeptides of N[3]-4-methoxyfumaryl-L-2,3-diaminopropanoic acid of the general formula

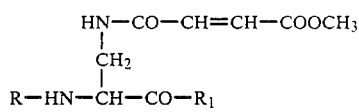

where R is a hydrogen atom when $R_1$ is the dipeptide residue containing the residue of alanine, methonine, valine, leucine or norvaline, or R and $R_1$ have the same meaning and are the residue of monoaminomonocarboxylic aminoacid, such as those of alanine, methionine, valine, leucine, or norvaline, or R is the dipeptide residue containing the residue of alanine, methionine, valine, leucine, norvaline, lysine, ornithine, sarcosine, 2,4-diaminobutanoic acid and 2,3-diaminopropanoic acid, and $R_1$ is a hydroxide group, and the method of their obtaining. The method of obtaining involves converting N[2]-tetrbutoxycarbonyl, N[3]-4-methoxyfumaroyl-L-2,3-diaminopropanoic acid into an active ester which is used for acylating a dipeptide or N[2]-tetr-butoxycarbonyl, N[3]-4-methoxyfumaryl-L-2,3-diaminopropanoic acid into an active ester which is used for acylating the aminoacid whereafter the protection of the amino group is removed and the latter is acylated with an active ester of the N-protected aminoacid or N[3]-4-methoxyfumaryl-L-2,3-diaminopropanoic acid is acylated with an active ester of the N-protected dipeptide and the protection of the amino group is removed from the obtained N-protected tripeptide in the medium of a non-polar organic solvent or its mixture with water, whereas the final product in the form of a salt is isolated by being crystallized or being converted into a free acid.

1 Claim, No Drawings

TRIPEPTIDES OF $N^3$-4-METHOXYFUMARYL-L-2,3-DIAMINO-PROPANOIC ACID

The subject of this present invention is tripeptides of $N^3$-4-methoxyfumaryl-L-2,3-diaminopropanoic acid of the general formula

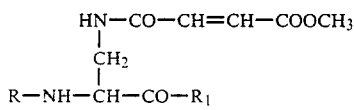

where R is a hydrogen atom when $R_1$ is a dipeptide residue containing a residue of alanine, methionine, valine, leucine, norvaline, or R and $R_1$ have the same meaning and mean the residues of monoaminomonocarboxylic aminoacid, such as that of alanine, methionine, valine, leucine, norvaline, or R is the residue of dipeptide containing the residues of alanine, methionine, valine, norvaline, lysine, ornithine, sarcosine, 2,4-diaminobutanoic acid and 2,3-diaminopropionic acid and $R_1$ is a hydroxyl group, and the method of their obtaining.

Dipeptides containing derivatives of L-2,3-diaminopropanoic acid are known until now and the method of their obtaining involves acylation of $N^3$-4-methoxyfumaryl-L-2,3-diaminopropionic acid with an active ester of N-protected aminoacid, the reaction taking place in the medium of an organic solvent at room temperature (R. Andruszkiewicz, H. Chmara, S. Milewski and E. Borowski, J. Med. Chem., 30, 17-15-1719/1987).

On the other hand, tripeptides are not known which show high antifungal activity and contain derivatives of L-2,3-diaminopropanoic acid.

The essence of this present invention are tripeptides of $N^3$-4-methoxyfumaryl-L-2,3-diaminopropanoic acid of the general formula

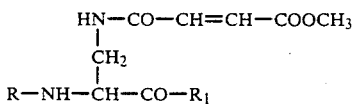

where R is a hydrogen atom when $R_1$ is a dipeptide residue containing the residue of alanine, methionine, valine, leucine, norvaline, or R and $R_1$ have the same meaning and mean the amino residue of monoaminomonocarboxylic amino acid, such as those of alanine, methionine, valine, leucine, norvaline, or R means the dipeptide residue containing the residue of alanine, methionine, valine, leucine, norvaline, lysine, ornithine, sarcosine, 2,4-diaminobutanoic acid and 2,3dipropanoic acid and $R_1$ means a hydroxide group.

According to this present invention the method of obtaining tripeptides of $N^3$-4-methoxyfumaryl-L-2,3-diaminopropanoic acid of the general formula

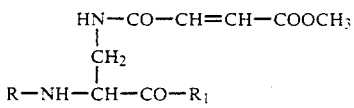

where R is a hydrogen atom and $R_1$ is the dipeptide residue containing the residue of alanine, methionine, valine, leucine, or norvaline involves converting of $N^2$-tertbutoxycarbonyl, $n^3$-4-methoxyfumaryl-L-2,3-diaminopropanoic to an active ester which is used for acylation of the dipeptide in the medium of a polar organic solvent or its mixture with water, whereas the final product in the form of a salt is isolated by being crystallised or converted into a free acid.

N-hydroxysuccinoimide is the agent activating $N^2$-tertbutoxycarbonyl, $N^3$-4-methoxyfumaryl-L-2,3-diaminopropionic acid.

Tetrahydroxyfurane or a mixture of a monohydric aliphatic alcohol with a C1–C5 chain length and water is used as an organic solvent.

According to this present invention, the method of obtaining tripeptides of $N^3$-4-methoxyfumaryl-L-2,3-diaminopropionic acid of the general formula

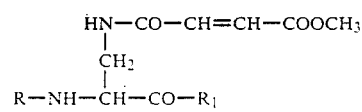

where $R_1$ and R are the residue of monoaminomonocarboxylic amino acid, such as these of alanine, methionine, valine, leucine or norvaline involves converting $N^2$-tert-butoxycarbonyl, $N^3$-4-methoxyfumaryl-L-2,3-diaminopropionic acid into an active ester which is used for acylating monoaminomonocarboxylic aminoacid whereafter the protection of the amino group is removed and the latter is acylated with an active ester of N-protected monoaminomonocarboxylic aminoacid in the medium of a polar organic solvent, or its mixture with water, whereas the final product in the form of a salt is isolated by being crystallised and, possibly, converted into a free acid.

N-hydroxysuccinoimide is an agent activating $N^2$-tert-butoxycarbonyl, $N^3$-4-methoxyfumaryl-L-2,3-diaminopropionic acid and N-protected monoaminocarboxylic aminoacid.

Tetrahydrofurane or a mixture of monohydric aliphatic alcohol with a C1–C5 chain length and water is used as a polar organic solvent.

According to this present invention, the method of obtaining tripeptides of $N^3$-4-methoxyfumaryl-L-2,3-diaminopropionic acid of the general formula

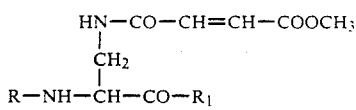

where R is the dipeptide residue containing the residue of alanine, methionine, valine, leucine, norvaline, lysine, ornithine, sarcosine, 2,4-diaminobutanoic acid and 2,3-diaminopropanoic acid and $R_1$ is a hydroxide group involves acylating $N^3$-4-methoxyfumaryl-L-2,3-diaminopropionic acid with an active ester of N-protected dipeptide in the medium of a polar organic solvent or its mixture with water, whereafter the amine group protection is removed from the tripeptide thus obtained and the final product in the form of a salt is isolated by being crystallised and, possibly, being converted into a free acid.

N-hydroxysuccinoimide is the agent activating the N-protected monoaminomonocarboxylic aminoacid.

Tetrahydrofuran or a mixture of monohydric (monohydroxyl) aliphatic alcohol with a C1–C5 chain length and water is used as a polar organic solvent. The compounds in question show an antimicrobial activity, patricularly an antifungal activity relating to pathogenic fungi, such as *Candida albicans, Cryptococens neoformans* and *Aspergillus spp.*, whereas their essential advantage is the observed lower frequency of occurrence of spontaneous mutants, microorganisms resistant to the action of tripeptides in comparison to the mutants resistant to the action of dipeptides.

The above has been assumed to be related to the difference in the specificity of action of the so-called permeases transporting peptides to cells of microorganisms.

The antifungal activity has been evaluated, by the example of $N^2$-L-methionyl-L-norvalyl-$N^3$-4-methoxyfumaryl-L-2,3-diaminopropanoic acid during the in vitro and in vivo tests conducted on experimentally infected mouse models.

The in vitro activity has been evaluated by the method of serial dilutions in parallel on solid YNB medium and on YNB w/o+AN medium, where the abbreviation AN means 200 mg of sodium glutamate, 10 mg of L-histidine, 20 mg of DL-methionine, 20 mg DL-tryptophane, 10 g of glucose and 15 g of agar-agar per 1 liter of the YNB medium. The application of the medium modified in such a manner was made necessary by the known phenomenon of lower biological activity in the media containing ammonium sulphate as a source of nitrogen.

In evaluating the activity allowance has been made for the value ranges of the minimum inhibitory concentrations the growth of strains (MIC in mg/liter), the cummulative percentages of the strains hampered by a definite mean geometric concentration of the value of MIC ($G_{MIC}$), the values of the concentrations hampering the growth of 50 and 90 per cent of the tested strains ($MIC_{50}$ and $MIC_{90}$) representing the species *Candida albicans* (n=50), other species of the genus Candida (Candida spp., n=117) and the entire genus Candida (n=167). 167 strains of the genus Candida have been freshly isolated from hospitalised patients. The table presented below shows the activity of $N^2$(-L-methionyl-L-norvalyl)$N^3$-(4-methoxyfumaryl)-L-2,3-diaminoproprionic acid for 167 strains of the genus Candida isolated from patients.

The derivatives show a high therapeutic efficiency. The therapeutic efficiency was evaluated by the example of $N^2$(-L-methionyl-L-norvalyl), $N^3$-4-methoxyfumaryl-L-2,3diaminopropanoic acid (Met-Nva-FMAP).

During the in vivo tests was used of the model of generalised candidiosis with the Swiss mouse. The mice were infected intravenously with the strain *Candida albicans* 162. The infecting dose amounted to $2 \times 10^7$ cfu per 1 gm of body weight. The therapeutic efficiency was evaluated by mathematically determining protective doses ($PD_{50}$), curative doses ($CD_{50}$), and by quantitative mycological evaluation of the kidneys of the Swiss mice infected with experimental *candidiase*.

By way of example, a protective dose, $PD_{50}$, of 0.374 mg/kg has been determined for the Met-Nva-FMAP tripeptide for 5–9 days of observation, whereas curative doses, $CD_{50}$, determined for 9 and 16 days of observation amounted to 0.499 and 1.062 mg/kg, respectively.

The quantitative evaluation of the kidneys of the nice infected and cured with a dose of $10 \times CD_{50}/g$, i.e. 4.99 mg/kg, of the Met-Nva-FFMAP tripeptide showed that the number of the cells of *Candida albicans* was markedly reduced on the 6th day as compared with a control group.

Tripeptides of $N^3$-4-methoxyfumaryl-L-2,3-diaminopropionic acid and the method of their obtaining are illustrated by the examples provided below.

EXAMPLE I a. 2.065 g/5 mM/ of N-hydroxysuccinoimide ester of $N^2$-t-butoxycarbonyl, $N^3$-4methoxyfumaryl-L-2,3-diaminopropanoic acid in 10 ml of tetrafurane are added to a solution of 1.1 g (5mM) L-methionyl-L-alanine and 0.42 g (5 mM) of sodium hydrogen carbonate in 15 ml of water under intensive mixing and are allowed to stand for 6 hours. Next, the solvent is evaporated, the residue dissolved in 10 ml of water and acidified with 1 N hydrochloric acid to pH=2 and the reaction product is taken up several times with ethyl acetate. The organic layer is washed with water, dried over anhydrous magnesium sulphate and evaporated. The residue is crystallised from ethyl acetate and hexane. The above results in 2.27 g of $N^2$-t-butoxycarbonyl,$N^3$-4-methoxyfumaryl-L-2,3-diaminopropanoyl-L-methionyl-L-alanine

| Species | Number of strains | Substrate | MIC value range, mg/liter /48 h - 37° C./ | $G_{MIC}$ | $MIC_{50}$ | $MIC_{90}$ |
|---|---|---|---|---|---|---|
| C. albicans | 50 | YNB | 0.006–100 | 39.5 | 120.1 | 180.6 |
| | | YNB w/O + AN | 0.006–100 | 3.3 | 0.6 | 149.8 |
| Candida spp. | 117 | YNB | 0.006–100 | 68.9 | 127.5 | 182.8 |
| | | YNB w/O + AN | 0.006–100 | 6.9 | 2.9 | 162.5 |
| Total | 167 | YNB | 0.006–100 | 58.3 | 125.4 | 182.2 |
| | | YNB w/O + AN | 0.006–100 | 5.5 | 1.4 | 159.4 |

For one of the elected strains of *Candida albicans* ATCC 26278, the minimum inhibitory concentration, MIC, amounted to 0.4 mg/liter in the case of $N^2$(-methionyl-L-norvalyl), $N^3$-methoxyfumaroyl-L-2,3-diaminopropanoic acid and to 0.02 mg/liter for $N^2$(-L-lysyl-L-norvalyl), $N^3$-4-methoxyfumaryl-L-2,3-diaminopropanoyl-L-2,3-diaminopropanoic acid.

with a melting point of 108°–110° C. being obtained, which amounts to 88 per cent of the theoretical yield.

b. 1.036 g (2 mM) of $N^2$-t-butoxycarbonyl, $N^3$-4-methoxyfumaryl-L-2,3-diaminopropanoyl-L-methionyl-L-alanine are dissolved in 10 ml of 4 N hydrogen chloride in dioxan and allowed to stand for 5 hours. Next, the solvents are evaporated and the residue is crystallised from a mixture of methanol and ethyl ether. 0.863 g of $N^3$-4-methoxyfumaryl-L-2,3-diaminopropanoyl-L-methionyl-L-aniline of a melting point of 178°–180° C. is obtained, which amounts to 99 per cent of the theoretical yield. MIC=0.1 ug/ml

EXAMPLES II–VII

Just as in Example I, the following derivatives of L-2,3-diaminopropanoic acid of the tripeptide structure have been obtained, as presented in the table below.

TABLE 1

| Example | Name of derivative | mass ion. m/z |
|---|---|---|
| II | $N^3$—4-methoxyfumaroyl-L-2,3-diaminopropanoyl-L-alanyl-L-alanine hydrochloride | 358 |
| III | $N^3$-4-methoxyfumaroyl-L-2,3-diaminopropanoyl-L-methionyl-L-methionine hydrochloride | 478 |
| IV | $N^3$-4-methoxyfumaroyl-L-2,3-diaminopropanoyl-L-valyl-L-alanine hydrochloride | 386 |
| V | $N^3$-4-methoxyfumaroyl-L-2,3-diaminopropanoyl-L-leucyl-L-leucine-hydrochloride | 442 |
| VI | $N^3$-4-methoxyfumaroyl-L-2,3-diaminopropanoyl-L-methionyl-L-valine hydrochloride | 446 |
| VII | $N^3$-4-methoxyfumaroyl-L-2,3-diaminopropanoyl-L-alanyl-L-methionine hydrochloride | 418 |

EXAMPLE VIII a. 2.065 g (5 mM) N-hydroxysuccinoimide ester $N^2$-t-butoxycarbonyl, $N^3$-4-methoxyfumaryl-L-2,3-diaminopropanoic acid in 10 ml of tetrafurane are added under intensive mixed to a cooled solution of 0.74 g (5 mM) of L-methionine an 0.42 g (5 mM) of sodium hydrogen carbonate in 10 ml of water and allowed to stand for 10 hours. Next, the solvent is evaporated, the residue dissolved in 10 ml of water and acidified with 1 N hydrochloric acid to a pH-value of 2, and the reaction product is several times extracted with ethyl acetate. The organic layer is washed with water, dried over anhydrous magnesium sulphate and evaporated. The residue is crystallised from ethyl acetate and hexane. 1.96 g of $N^2$-t-butoxycarbonyl, $N^3$-4-methoxyfumaryol-L-2,3-diaminopropanoyl-L-methionine with a melting point of 84°–86° C. are obtained, which accounts for 89 per cent of the theoretical yield.

b. 0.89 g (2 mM) of $N^2$-t-butoxycarbonyl, $N^3$-4-methoxyfumaryl-L-2,3 diaminopropanoyl-L-methionine is dissolved in 10 ml of 4 N hydrogen chloride in dioxan and is allowed to stand for 3 hours at room temperature. Next, the solvents are evaporated and the residue crystallised from a mixture of methanol and ethyl ester. 0.714 g of $N^3$-4-methoxyfumaryl-L-2,3-diaminopropanoyl-L-methionine hydrochloride with a melting point of 184°–186° C. is obtained, which amounts to 94 per cent of the theoretical yield.

c. 0.381 g /1 mM/ $N^3$-4-methoxyfumaryl-L-2,3-diaminopropanoyl-L-methionine hydrochloride is dissolved in 10 ml of methanol cooled down to a temperature of 0° C. and 0.3 ml of triethylamine is added. 0.346 g (1 mM) of N-hydroxysuccinoimide N-t-butoxycarbonyl-L-methionine dissolved in 10 ml of tetrahydrofuran is added to that solution under intensive mixing and the reaction mixture is allowed to stand for 5 hours. The further procedure is the same as in Example I. 0.485 g of $N^2$-/N-t-butoxycarbonyl-L-methionyl/, $N^3$-4-methoxyfumaryl-L-2,3-diaminopropanoyl-L-methionine with a melting point of 148°–150° C. is obtained, which amounts to 84 per cent of the theoretical yield.

d. 0.298 g (0.5 mM) $N^2$-(N-t-butoxycarbonyl-L-methionyl), $N^3$-4-methoxyfumaryl-L-2,3-diaminopropanoyl-L-methionine is dissolved in 10 ml of 4 N hydrogen chloride in dioxan and is allowed to stand for 4 hours at room temperature. Thereafter, the solvents are evaporated and the residue is crystallised from a mixture of methanol and ethyl ether. 0.246 g of $N^2$-L-methionyl, $n^3$-4-methoxyfumaryl-L-2,3-diaminopropanoyl-L-methionine hydrochloride with a melting point of 205°–207° C. is obtained, which amounts to 96 per cent of the theoretical yield.

The MIC is 0.8 μg/ml.

EXAMPLES IX–XIV

Just as in Example XIII the following derivatives of L-2,3-diaminopropionic acid, having the tripeptide structure and presented in Table 2, have been obtained.

TABLE 2

| Example | Name of derivatives | mass ion. m/z |
|---|---|---|
| IX | $N^2$—L-alanyl-, $N^3$-4-methoxyfumaroyl-L-2,3-diaminopropanoyl-L-methionine hydrochloride | 418 |
| X | $N^2$—L-alanyl, $N^3$-4-methoxyfumaroyl-L-2,3-diaminopropanoyl-L-alanine hydrochloride | 358 |
| XI | $N^2$—L-methionyl, $N^3$-4-methoxyfumaroyl-L-2,3-diaminopropanoyl-L-alanine hydrochloride | 418 |
| XII | $N^2$—L-valil, $N^3$-4-methoxyfumaroyl-L-2,3-diaminopropanoyl-L-valine-hydrochloride | 414 |
| XIII | $N^2$—L-leucyl, $N^3$-4-methoxyfumaroyl-L-2,3-diaminopropanoyl-L-alanine hydrochloride | 400 |
| XIV | $N^2$-methionyl, $N^3$-4-methoxyfumaroyl-L-2,3-diaminopropanoyl-L-leucine hydrochloride | 460 |
| XV | $N^2$—L-norvalyl, $N^3$-4-methoxyfumaroyl-L-2,3-diaminopropanoyl-L-norvaline hydrochloride | 414 |

EXAMPLE XVI a. 0.7 ml of triethylamine and 1.27 g (5 mM) of $n^3$-4-methoxyfumaryl-L-2,3-diaminopropanoic hydrochloride dissolved in 5 ml of water is added to a cooled solution of 1.57 g (5 mM) of N-hydroxysuccinimide ester of N-tert-butoxycarbonyl-L-norvaline in 20 ml of tetrahydrofurane under intensive mixing. The whole is mixed for 4 hours and the solvent is evaporated. The residue is dissolved in 10 ml of water, 1 N hydrochloric acid is added until a pH-value of 2 has been obtained and the reaction product is extracted several times with ethyl acetate. The organic layer is washed with water, dried over anhydrous magnesium sulphate and the solvent is evaporated. The product is crystallised from a mixture of ethyl acetate and hexane.

1.7 g of $N^2$-t-butoxy carbonyl-L-norvalyl, $N^3$-4-methoxyfumaroyl-L-2,3-diaminopropanoic acid or melting point of 68°–70° C. is obtained, which amounts to 83 per cent of the theoretical yield.

b. 0.83 g (2 mM) of $N^2$-t-butoxycarbonyl-L-norvalyl, $N^3$-4-methoxyfumaroyl-L-2,3-diaminopropanoic acid is dissolved in 10 ml of 4 N hydrogen chloride in dioxan and allowed to stand for 4 hours at room temperature. Thereafter, the solvent is evaporated under reduced pressure and the residue is crystallised from a mixture of methanol and ethyl ether.

0.65 g of $N^2$-L-norvalyl, $N^3$-4-methoxyfumaryl-L-2,3-diaminopropanoioacidhydrochloride with a melting point of 188°–190° C. is obtained, which amounts to 93 per cent of the theoretical yield.

c. 0.3 ml of triethylamine and 0.351 g of (1 mM) $N^2$-L-norvalyl, $N^3$-2-methoxyfumaroyl-L-2,3-diaminopropanoic hydrochloride dissolved in 10 ml of water are added to a cooled solution of 0.346 g (1 mM) N-hydroxysuccinoimide ester of N-t-butoxycarbonyl-L-methionine in 10 ml of tetrahydrofuran. The whole is mixed for 4–6 hours and the solvent is evaporated. The residue is dissolved in 10 ml of water, 1 N hydrochloric acid is added until pH=2 has been obtained and the reaction product is extracted with ethyl acetate. The organic layer is washed with water, dryed over magnesium sulphate and the solvent is evaporated. The product is crystallised from a mixture of ethyl ether and cyclohexane.

0.415 g of $N^2$-(N-t-butoxycarbonyl-L-methionyl-L-norvalyl), $N^3$-4-methoxyfumaryl-L-2,3-diaminopropanoic acid with a melting point of 118°–120° C. is obtained, which amounts to 76 per cent of the theoretical yield.

d. 0.273 g (0.5 mM) $N^2$-(N-t-butoxycarbonyl-L-methionyl-L-norvalyl), $N^3$-4-methoxyfumaryl-L-2,3-diaminopropanoic acid is dissolved in 5 ml of 4 N hydrogen chloride in dioxan and is allowed to stand at room temperature. Thereafter, the solvent is evaporated under reduced pressure and the residue is crystallised from a mixture of methanol and ethyl ether.

0.23 g of $N^2$-L-methionyl-L-norvalyl, $N^3$-4-methoxyfumaryl-L-2,3-diaminopropanoic hydrochloride with a melting point of 190°–192° C. is obtained, which amounts to 95 per cent of the theoretical yield. The MIC is 0.8 μg/ml.

EXAMPLES XVII–XXV

Just as in Example XV the following derivatives of L-2,3-diaminopropanoic acid, having the structure of tripeptides and presented in the table below, have been obtained.

| Example | Name of derivative | Mass ion, m/z |
|---|---|---|
| XVII | $N^2$—L-methionyl-L-alanyl, $N^3$-4-methoxyfumaroyl-L-2,3-diaminopropanoic hydrochloride | 418 |
| XVIII | $N^2$-sarcosyl-L-norvalyl, $N^3$-4-methoxyfumaroyl-L-2,3-diaminopropanoic hydrochloride | 404 |
| XIX | $N^2$—L-leucyl-L-alanyl, $N^3$-4-methoxyfumaroyl-L-2,3-diaminopropanoic hydrochloride | 400 |
| XX | $N^2$—L-valyl-L-methionyl, $N^3$-4-methoxyfumaroyl-L-2,3-diaminopropanoic hydrochloride | 446 |
| XXI | $N^2$—L-norvalyl-L-norvalyl, $N^3$-4-methoxyfumaroyl-L-2,3-diaminopropanoic hydrochloride | 414 |
| XXII | $N^2$—L-lysyl-L-norvalyl-$N^3$-4-methoxyfumaryl-L-2,3-diaminopropanoic dihydrochloride | 443 |
| XXIII | $N^2$—L-ornithyl-L-norvylyl-$N^3$-4-methoxyfurmaryl-L-2,3-diaminopropanoic dihydrochloride | 429 |
| XXIV | $N^2$-L-2,4-diaminobutanoyl-L-norvalyl-$N^3$-4-methoxyfumaroyl-L-2,3-diaminopropanoic dihydrochloride | 415 |
| XXV | $N^2$—L-2,3-diaminopropanoyl-L-norvalyl-$N^3$-4-methoxyfumaroyl-L-2,3-diaminopropanoic dihydrochloride | 401 |

We claim:

1. A tripeptide of $N^3$-4-methoxyfumaryl-L-2,3-diaminopropanoic acid of the general formula

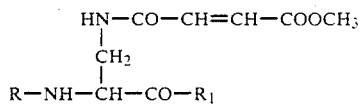

where R is a hydrogen atom when $R_1$ is the dipeptide residue containing the residue of alanine, methionine, valine, leucine, norvaline, or R and $R_1$ have the same meaning and are the residue of monoaminomonocarboxylic aminoacid, selected from the group consisting of alanine, methionine, valine, leucine, norvaline, or R is the dipeptide residue containing the residue of alanine, methionine, valine, leucine, norvaline, lysine, ornithine, sarcosine, 2,4-diaminobutanoic acid and 2,3-diaminopropanoic acid, and $R_1$ is a hydroxide group.

* * * * *